(12) United States Patent
Perouse

(10) Patent No.: US 6,827,736 B2
(45) Date of Patent: Dec. 7, 2004

(54) TUBULAR ENDOPROSTHESIS COMPRISING A DEFORMABLE COLLAR AND OPERATING KIT FOR ITS IMPLANTATION

(75) Inventor: Eric Paul Perouse, Paris (FR)

(73) Assignee: Laboratories Perouse, Bornel (FR)

( * ) Notice: Subject to any disclaimer, the term of this patent is extended or adjusted under 35 U.S.C. 154(b) by 74 days.

(21) Appl. No.: 10/101,924

(22) Filed: Mar. 21, 2002

(65) Prior Publication Data

US 2002/0156517 A1 Oct. 24, 2002

(30) Foreign Application Priority Data

Mar. 23, 2001 (FR) .............................. 01 03975

(51) Int. Cl.⁷ .................................................. A61F 2/06
(52) U.S. Cl. ..................................... 623/1.36; 623/1.23
(58) Field of Search .............................. 623/1.11, 1.13, 623/1.16, 1.23, 1.27, 1.35, 1.36

(56) References Cited

U.S. PATENT DOCUMENTS 5,868,777 A    2/1999   Lam
6,051,020 A  * 4/2000   Goicoechea et al. ........... 623/1
6,475,238 B1 * 11/2002  Fedida ....................... 623/1.16
6,520,987 B1 * 2/2003   Plante ....................... 623/1.16

FOREIGN PATENT DOCUMENTS

| WO | 98/19629 | 5/1998 |
| WO | 98/19630 | 5/1998 |
| WO | 99/18887 | 4/1999 |
| WO | 99/38454 | 8/1999 |
| WO | 00/41632 | 7/2000 |
| WO | 00/69364 | 11/2000 |

* cited by examiner

Primary Examiner—David H. Willse
Assistant Examiner—Hieu Phan
(74) Attorney, Agent, or Firm—Wenderoth, Lind & Ponack, L.L.P.

(57) ABSTRACT

A tubular endoprosthesis (10) having a flexible tubular skirt (12) designed to channel a body fluid. The endoprosthesis includes a collar (14) for connection of the skirt (12) through a lateral wall (110) of a tubular conduit (108). The connection collar (14) is initially joined to one end of the skirt (12) and has, at its periphery, elements (34) for securing it to the wall (110). The securing elements (34) are deformable between an initial docking position and a final connection position.

31 Claims, 6 Drawing Sheets

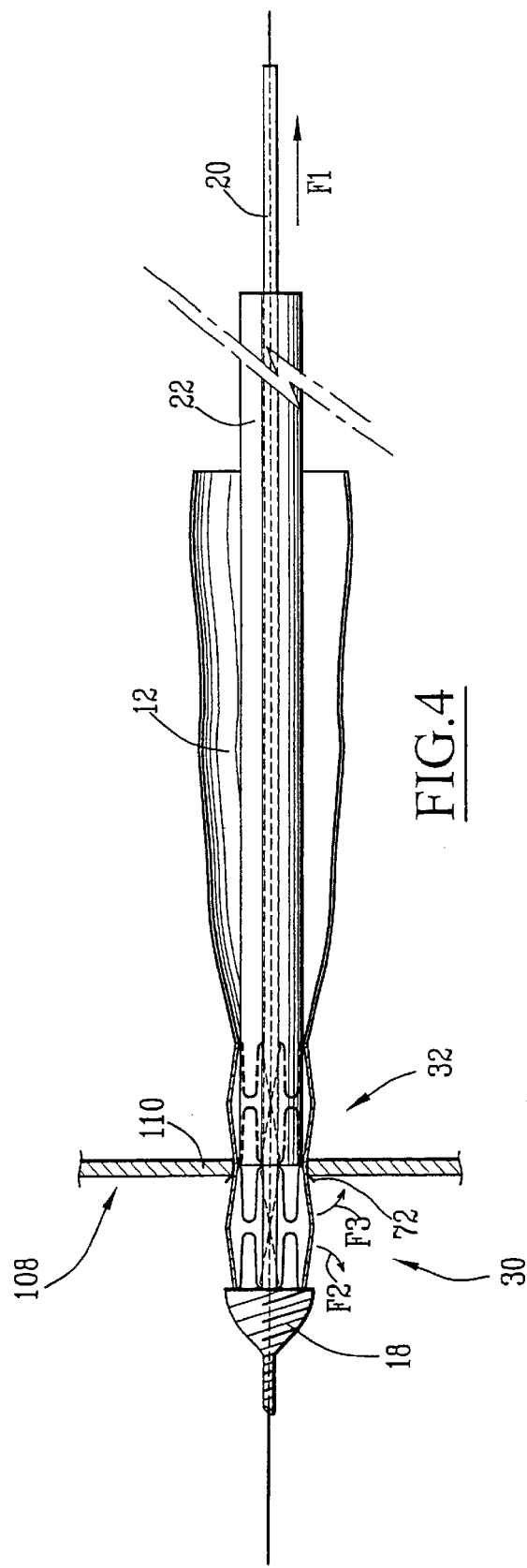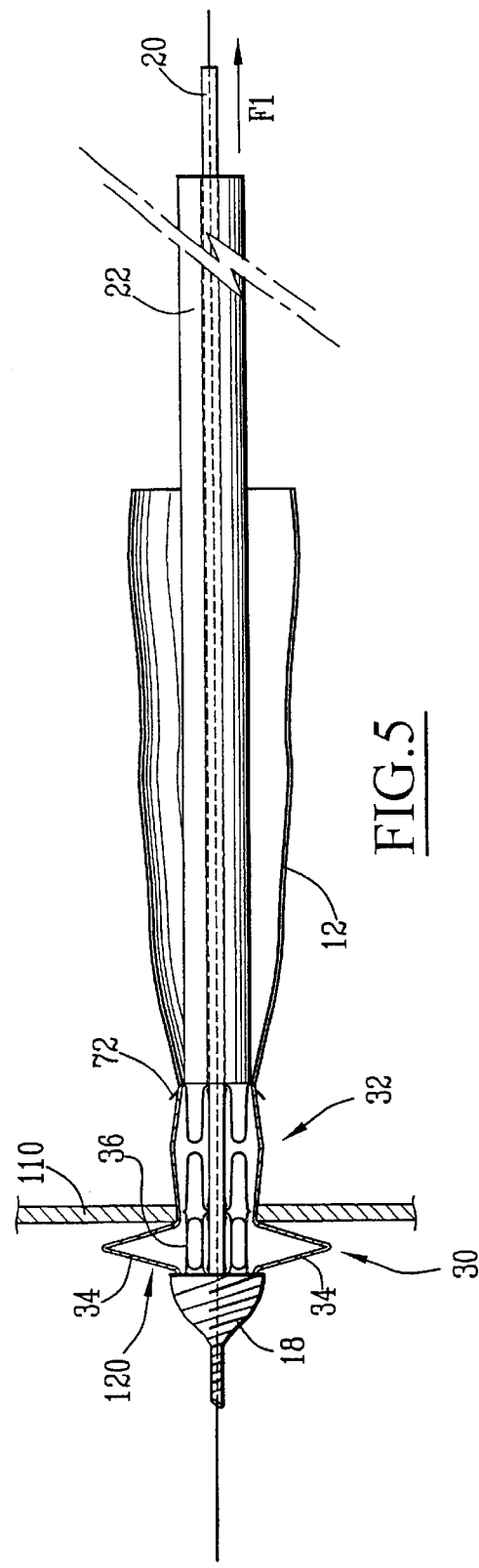

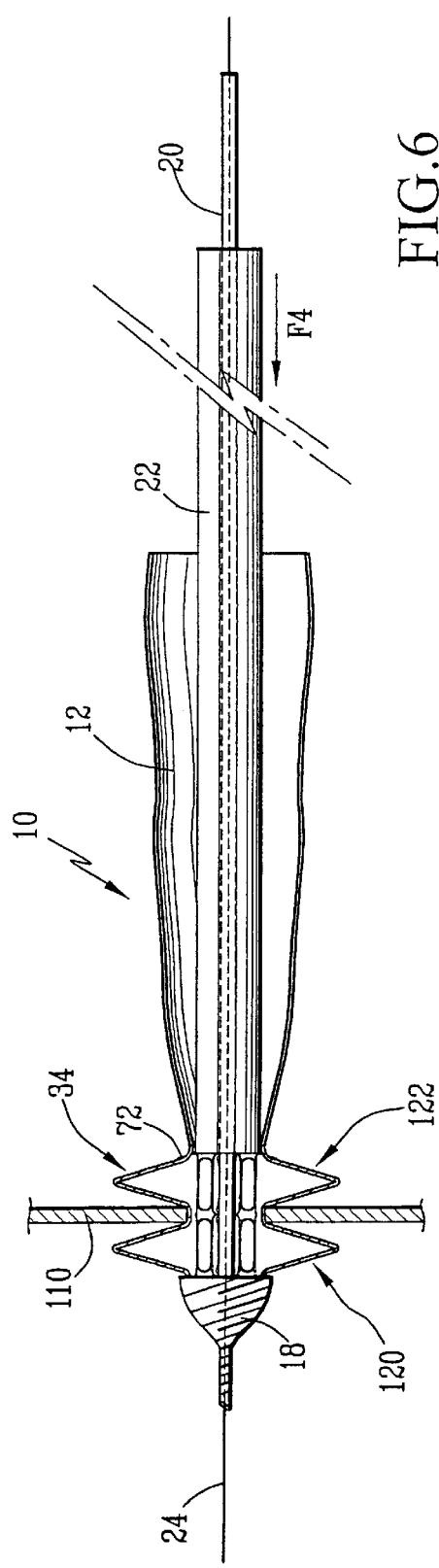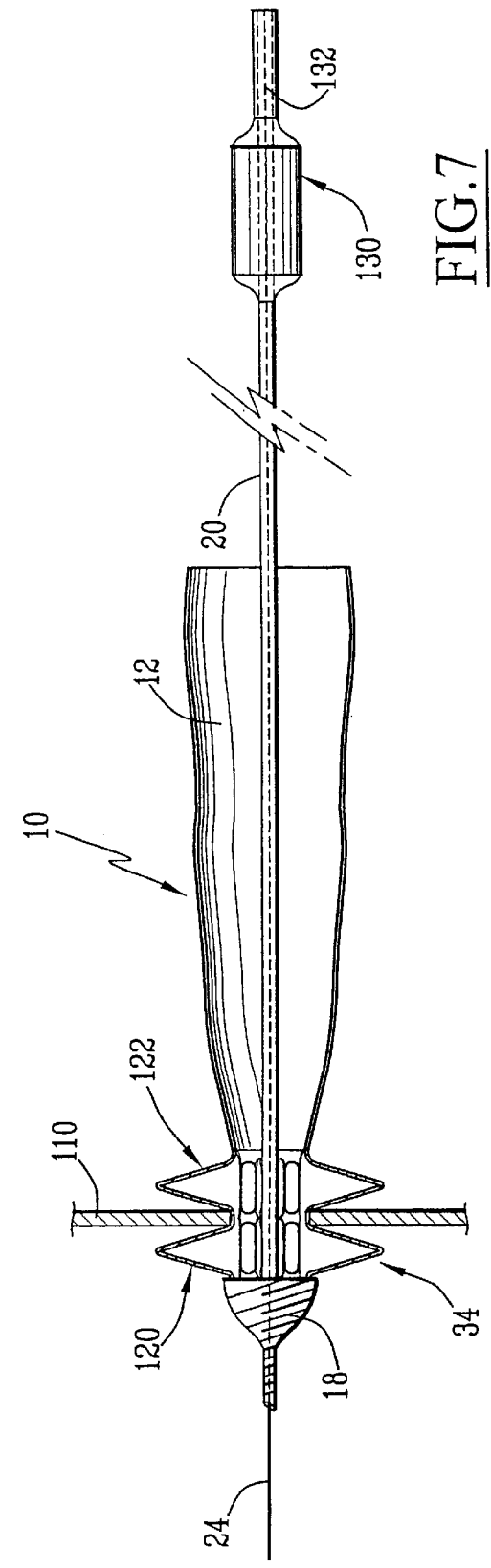

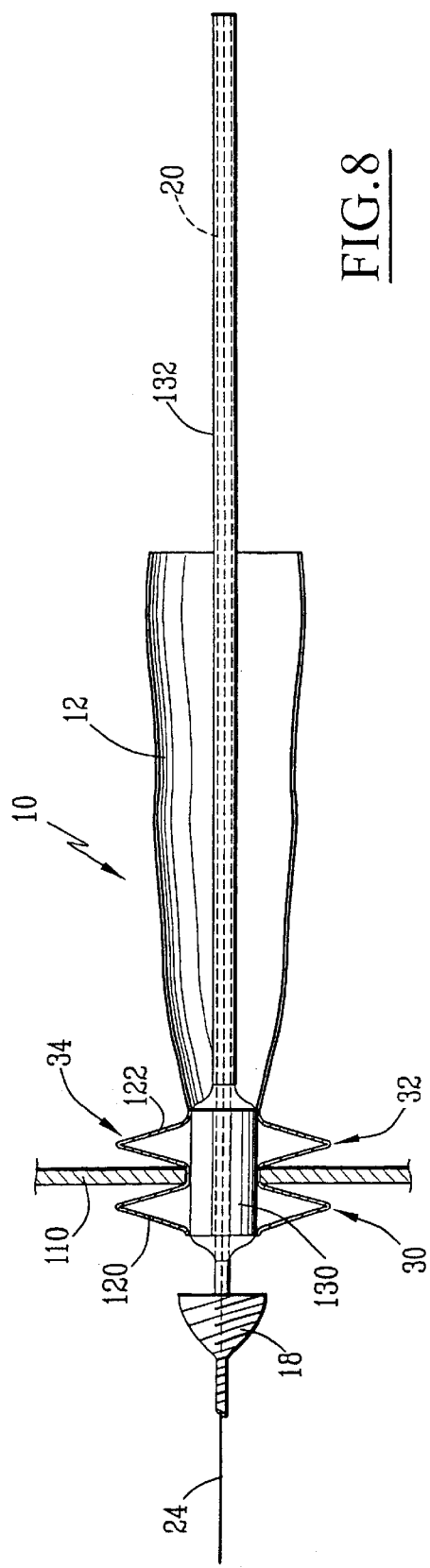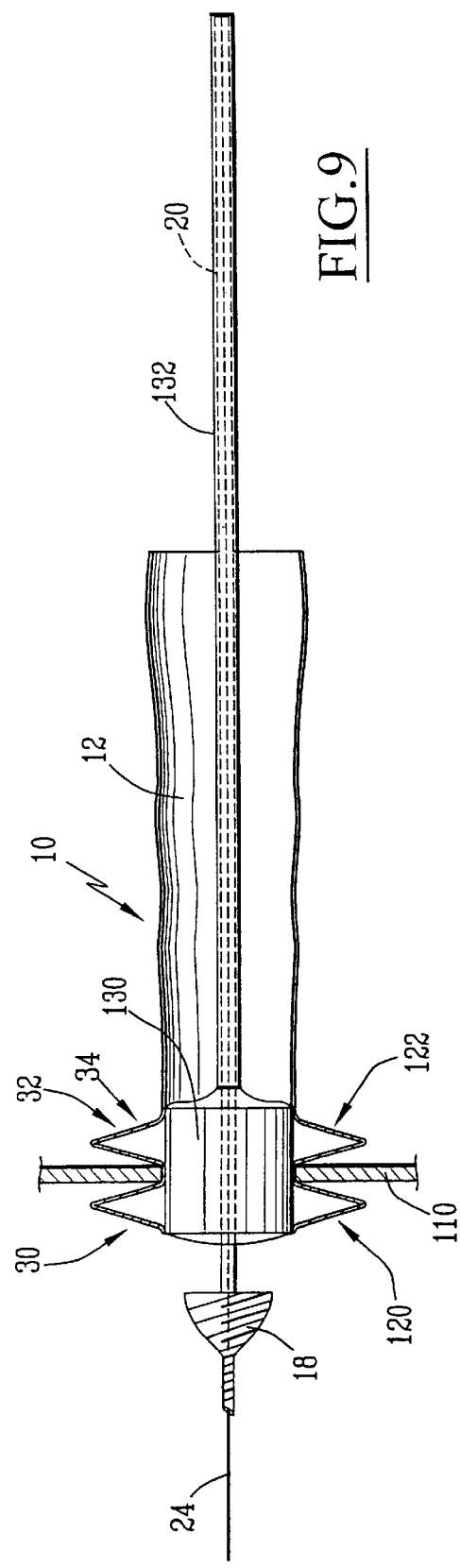

TUBULAR ENDOPROSTHESIS COMPRISING A DEFORMABLE COLLAR AND OPERATING KIT FOR ITS IMPLANTATION

BACKGROUND OF THE INVENTION

1. Field of Invention

The present invention relates to a tubular endoprosthesis, of the type comprising a flexible tubular skirt designed to channel a body fluid.

2. Description of Related Prior Art

At present it is known practice to treat aneurysms of the arterial or venous network by fitting an endoprosthesis in the region of a widened diameter of the network. In order to lessen the impact of the surgical intervention on the patient, it is known to perform celioscopic surgery or endoluminal surgery. In this technique, the surgeon operates inside the body via a small orifice through which the instruments are introduced, thereby avoiding the need to make a large incision in the region to be operated on.

For endoluminal treatment of aneurysms situated in immediate proximity to a bifurcation of the arterial or venous network, it is known to fit an endoluminal prosthesis which has a general Y-shape. This endoprosthesis comprises a trunk which extends through the aneurysm. The trunk is continued by two branches, each being introduced into a derivation situated near the aneurysm.

In the endoluminal intervention for fitting the Y-shaped prosthesis, the prosthesis is first introduced by way of a catheter into the network to be treated, the prosthesis being in a folded-up position.

The surgeon then has to deploy the prosthesis when the latter has been released from the catheter in the aneurysm.

The positioning of the trunk of the prosthesis and of each of its branches in the two bifurcations of the arterial or venous network is an extremely delicate operation for the surgeon since he has to operate remotely using long filiform instruments introduced into the network, and he must do this without a direct view of the operating site.

SUMMARY OF THE INVENTION

The object of the invention is to make available an endoprosthesis and an endoluminal operating kit permitting treatment of an aneurysm situated in proximity to a derivation, without the surgeon having excessive difficulty in fitting the endoprosthesis.

To this end, the invention concerns a tubular endoprosthesis of the aforementioned type, characterized in that it comprises a collar for connection of the skirt through a lateral wall of a tubular conduit. The connection collar is initially joined to one end of the skirt and has, at its periphery, elements for securing it to the wall. The securing elements are deformable between an initial docking position and a final connection position.

According to particular embodiments, the endoprosthesis includes one or more of the following characteristics:

- the securing elements are designed to bear against a face of the wall in their final connection position;
- the securing elements are elements which are plastically deformable from their initial docking position to their final connection position;
- the securing elements are elements with centrifugal radial expansion from their initial docking position to their final connection position;
- each securing element comprises an arm which has two consecutive segments joined to one another via a region of articulation, and each arm is deformable from an initial docking position, in which the two segments are spaced apart and extend substantially along a generatrix of the endoprosthesis, to a final connection position in which the two segments are folded in towards one another;
- the collar has at least two continuous rings which are centered on the axis of the endoprosthesis and to which each of the securing elements is joined, and the rings are displaceable axially between a spaced-apart position, in which the securing elements are in their initial docking position, and a closed-together position in which the securing elements are in their final connection position;
- the connection collar has plastically deformable bridges designed for radial expansion of the connection collar from a first configuration, in which the connection collar has an initial diameter, to a second configuration in which the connection collar has a diameter greater than its initial diameter;
- the plastically deformable bridges each have a general arch shape and extend along the periphery of the connection collar, which bridges are deformable from an initial position, in which each arch is closed, the connection collar being in its first configuration, and a final position in which each arch is opened, the connection collar being in its second configuration; and
- the connection collar comprises, axially, first and second successive crowns which continue the tubular skirt, each crown having securing elements, the elements of the first crown being designed to cooperate with the inner face of the wall of the tubular conduit, and the elements of the second crown being designed to cooperate with the outer face of the wall of the tubular conduit.

The invention also concerns an endoluminal operating kit comprising an endoprosthesis as defined above, a filiform pusher designed to cooperate with the connection collar, and a filiform member for retention of the connection collar.

According to particular embodiments, the endoluminal operating kit includes one or more of the following characteristics:

- it additionally comprises a toroidal inflatable balloon with radial expansion; and
- it additionally comprises a first endoprosthesis intended to form the tubular conduit to which the tubular endoprosthesis is fastened.

Finally, it concerns a bifurcated bypass prosthesis comprising a first endoprosthesis to which an endoprosthesis as defined above is connected.

BRIEF DESCRIPTION OF THE DRAWINGS

The invention will be better understood from reading the following description which is given solely by way of example and in which reference is made to the drawings, in which:

FIGS. 4, 5, 6, 7, 8 and 9 are elevation views of the endoprosthesis according to the invention during successive phases of the positioning operation;

DETAILED DESCRIPTION OF THE INVENTION

Figure 1:
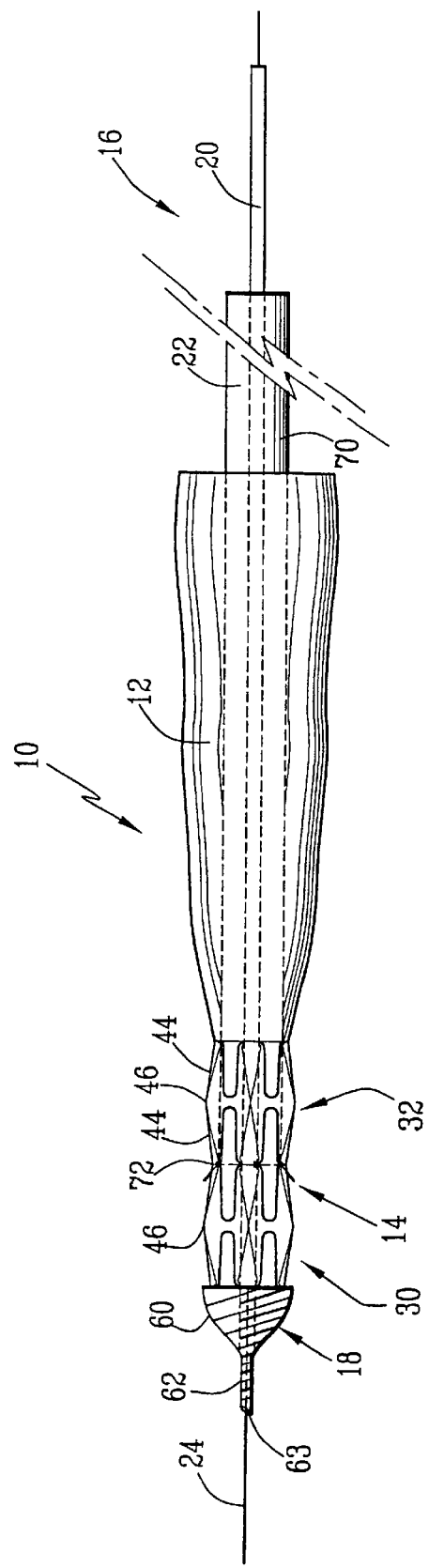
FIG. 1 is an elevation view of an endoprosthesis according to the invention.

In FIG. 1, an endoprosthesis according to the invention is shown before implantation. This endoprosthesis is intended to be connected in vivo to a first tubular endoprosthesis which has been fitted beforehand by endovascular surgery. This first endoprosthesis is, for example, made of a metal lattice embedded in a polymer film.

The endoprosthesis according to the invention can also be connected to an existing vessel by celioscopic surgery, that is to say by being attached from outside of the vessel.

The endoprosthesis illustrated in FIG. 1 is designed to be connected through the lateral wall of the already installed endoprosthesis, in order to constitute a branch of this endoprosthesis or an artery. The two endoprostheses joined together thus constitute a Y-shaped tubing in the aneurysm, forming a bifurcated bypass prosthesis.

The endoprosthesis according to the invention illustrated in FIG. 1 comprises a tubular skirt 12, at one end of which a plastically deformable connection collar 14 is secured.

Before implantation, the endoprosthesis is combined with positioning equipment 16 comprising an endpiece 18 mounted at the end of the collar and integral with a tube 20. This tube runs right through the endoprosthesis and has a length which is sufficient to allow it to be manipulated from its free end outside the body. The positioning equipment additionally comprises a filiform instrument 22 forming a pusher which is designed to ensure plastic deformation of the collar 14, retained by the endpiece 18, from the tube 20. This instrument 22 also has a length which is sufficient to allow it to be manipulated from outside the body.

As is illustrated in FIG. 1, the endoprosthesis 10 and the positioning equipment 16 are engaged on a surgical guide 24 passing axially right through the endoprosthesis.

The tubular skirt 12 of the endoprosthesis is formed, for example, of knitted textile fibers constituting a flexible tubular conduit.

The tubular skirt 12 axially continues the connection collar 14. One end of the skirt is, for example, sewn to the periphery of the end of the collar 14.

Figure 2:
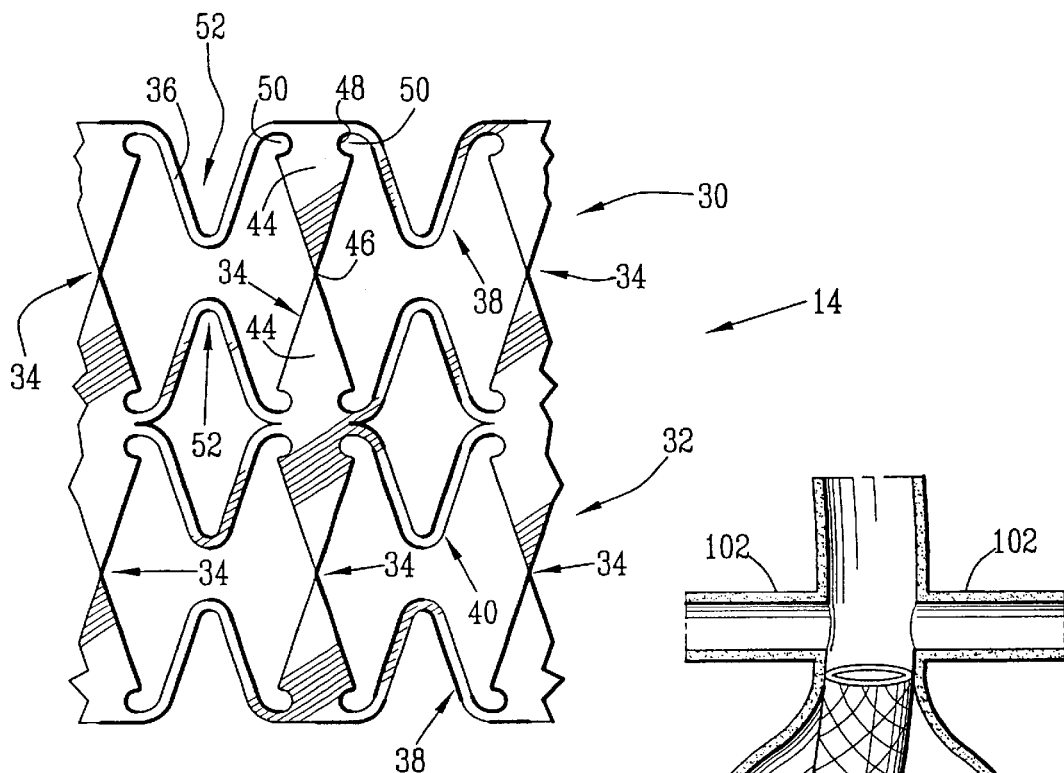
FIG. 2 is a detailed view of a portion of the connection collar of the endoprosthesis in FIG. 1.

Part of the connection collar 14 is represented in detailed form in FIG. 2. In this figure, it is represented before plastic deformation, that is to say before the endoprosthesis is fitted. The collar is thus in its initial docking position.

The collar 14 is formed, for example, from a tube of type 316L stainless steel. To form the collar, the lateral wall of the tube is cut out, for example by laser beam, in order to define plastically deformable metal portions, these portions are joined to one another via their ends. Thus, all the elements of the collar 14 are made from one piece.

The initial external diameter of the collar 14 is 5 mm, for example.

The collar 14 comprises, axially, two successive crowns 30 and 32. These two crowns are identical and are joined to one another in the middle region of the collar.

Each crown 30, 32 has a set of adjacent arms 34 whose length initially extends generally along a generatrix of the collar. The arms 34 constitute plastically deformable elements for securing the collar 14 to the wall of the first endoprosthesis which has initially been implanted. Thus, the arms 34 function as securing elements.

The adjacent ends of the arms 34 of the same crown 30, 32 are joined via plastically deformable bridges 36 together constituting a ring connecting the ends of the arms of that crown.

Thus, and as is illustrated in FIG. 2, the collar 14 comprises two end rings 38 and two median rings 40. The latter are arranged in the region of connection of the crowns 30 and 32.

The rings 38 and 40 are centered along the axis of the collar 14, that is to say along the axis of the endoprosthesis 10.

The arms 34 of the two crowns 30 and 32 are arranged in the continuation of one another so that the arms 34 of the two crowns extend in pairs along the same generatrix of the collar. Likewise, the bridges 36 of the four connecting rings 38 and 40 are arranged in alignment, four by four, along a generatrix of the collar.

Each arm 34 comprises two successive segments 44, of which the ends of reduced width are joined to one another via a region of articulation 46.

Each segment 44 of the same arm has a width decreasing progressively from its end joined to the connecting ring 38 or 40 towards the region of articulation 46. Thus, each arm has a generally biconical shape.

At its ends connected to the rings 38 and 40, each arm 34 has a region of reduced width 48. This region 48 is bordered by two lateral notches 50. It constitutes a region of articulation permitting centrifugal radial folding of the arm in relation to the axis of the ring.

The bridges 36 connecting the adjacent ends 48 of the arms of the same crown define arches 52 constituting open loops, each formed in a defined interval between two adjacent arms 34. These arches 52 extend in the general cylindrical envelope of the collar.

The arches 52 are each generally U-shaped. Each arch is linked to the rest of the collar only at each of its ends.

Each of the arches 52 is directed towards the median region of each crown 30, 32 in which it is integrated.

Initially, while the collar is in a first configuration and has a small diameter, the arch formed by each bridge 36 is closed. These bridges are plastically deformable in order to bring the collar into a second configuration where it has a diameter greater than its initial diameter and where each arch defined by a bridge is opened.

Initially, and as is illustrated in FIG. 1, the arms 34 of each crown 30, 32 are in a docking position. In this position, the arms are only very slightly deformed outwards so that the region of articulation 46 connecting the two segments of each arm projects in relation to the general cylindrical envelope of the collar, and in particular in relation to the cylindrical envelope containing the four connecting rings 38 and 40.

In the positioning equipment 16, the endpiece 18 is generally generated by revolution. It comprises a frustoconical portion 60. Its diameter decreases progressively from the connection collar 14 towards its free end. At this end, the frustoconical portion 60 is continued by a tubular portion 62 of smaller diameter, the free end of which is bevelled to form a perforating point 63.

The outer lateral surface of the endpiece 18 has a thread which allows the endpiece 18 to be used as a screw tap for perforating a wall.

The endpiece 18 is connected permanently to an end of the tube 20.

The end of the collar 14 remote from its end to which the skirt 12 is joined is engaged inside the frustoconical portion 60 of the endpiece 18. The collar 14 is initially held there by engagement.

The filiform instrument 22 constitutes a pusher. It comprises a tubular sleeve 70 within which the tube 20 extends axially. The sleeve 70 has a diameter smaller than the internal diameter of the collar 14 in order to be able to move axially therein. The tube 20 and the sleeve 70 can slide axially in relation to one another.

At its end engaged in the connection collar 14, the sleeve 70 is continued by claws 72 which project radially outwards. These claws 72 are designed to engage at the base of the arms 34, in the region 48 of reduced width delimited between the notches 50. In particular, these claws are designed to be engaged in the notches 50.

The claws 72 are designed in such a way as to bear against the contours of the collar 14 when the pusher 22 is displaced towards the endpiece 18, and to disengage from the contours of the collar 14 when the pusher 22 is pulled away from the endpiece 18. For this purpose, the claws 72 are formed, for example, by tongues which project radially outwards, these tongues being inclined towards the endpiece 18 from their region of connection to the sleeve 70 towards their free end.

The endoprosthesis 10 according to the invention is positioned in the following way.

Figure 3:
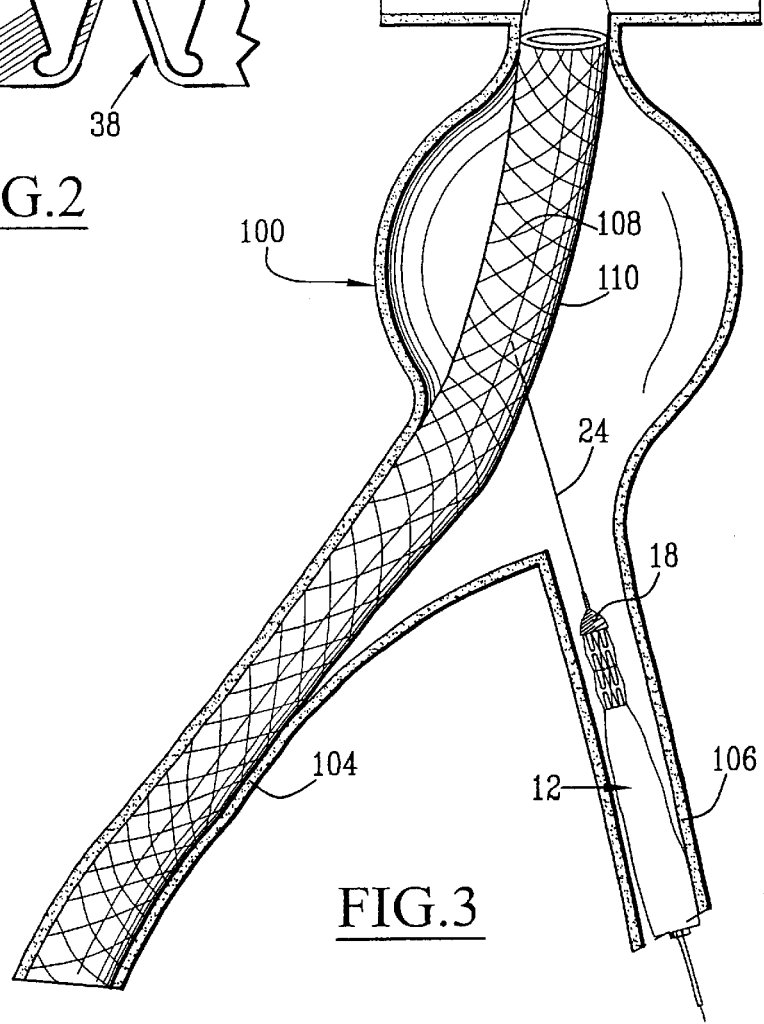
FIG. 3 is a schematic view of the initial phase of positioning the endoprosthesis in an aneurysm.

FIG. 3 shows the aorta and the two iliac arteries. These have an aneurysm 100 formed between the renal arteries 102 and two iliac bifurcations 104, 106 formed respectively by the right iliac artery and the left iliac artery.

To perform a bi-iliac aortic bypass of the aneurysm 100, a first tubular endoprosthesis 108 is firstly placed by any suitable known technique between the main section of the artery and the iliac bifurcation 104. The first endoprosthesis 108 thus extends through the aneurysm 100.

The endoprosthesis 108 is advantageously made of a tubular metal latticework embedded in a film which is extensible and is impermeable to liquids, for example an elastomer. The metal latticework is made of stainless steel with resilient properties, so that the first endoprosthesis 108 is self-expanding.

Such an endoprosthesis is often referred to as a covered stent.

As is known per se, the first endoprosthesis is able to deform spontaneously from a compressed state, in which it has a small diameter, to a dilated state, in which it has a greater diameter, this dilated state constituting its state at rest.

In the illustrated embodiment, and advantageously, the tubular latticework is made up of metal wires braided in interlocking helices wound in opposite directions. Thus, the tubular latticework delimits meshes formed as deformable rhombi.

On account of its inherent elasticity, the endoprosthesis 108 is held inside the arterial conduit by means of its natural radial expansion which ensures that it bears against the inner lateral surface of the conduit.

The endoprosthesis 10 according to the invention is intended to be engaged in the iliac artery 106 and to be connected radially to the first endoprosthesis 108 previously installed.

To position the endoprosthesis 10, and as is illustrated in FIG. 3, the surgical guide 24 is first engaged inside the artery 106 through an incision made, for example, in the patient's leg. The surgical guide is introduced into the artery until its end perforates the wall, labelled 110, of the first endoprosthesis 108 previously installed. The surgeon monitors the positioning of the surgical guide by suitable medical imaging measures. For easy perforation of the first endoprosthesis 108, the guide 24 is advantageously chosen to be rigid and stiff.

The endoprosthesis 10 is then engaged on the surgical guide 24 installed beforehand. It is moved gradually along into the artery 106, by pushing on the tube 20. The tube 20 thus acts on the endpiece 18 to which the endoprosthesis 10 is initially attached, thereby entraining the latter along the surgical guide 24.

From its position illustrated in FIG. 3, the endoprosthesis 10 is pushed until the end of the endpiece 18 bears against the lateral surface of the first endoprosthesis 108.

The endoprosthesis 10 is then rotated manually about the surgical guide 24 by manual actuation of the tube 20 by the surgeon. Under the action of the rotation of the endpiece 18 and the push exerted on the tube 20, the lateral wall 110 of the first endoprosthesis is gradually pierced by the screw-tap profiles formed on the endpiece 18.

The endoprosthesis 10 is then engaged through the wall 110 of the first endoprosthesis until it assumes the position illustrated in FIG. 4. In this position, the connection collar 14 extends in equal parts on either side of the wall 110. The connection collar 14 is positioned under visual monitoring using suitable medical imaging measures. To do this, all the parts constituting the endoprosthesis 10 are radiopaque.

Thus, the connecting rings 40 are brought substantially into the plane of the wall 110.

To permit the engagement of the collar 14, the mesh of the wall 110 through which the collar is engaged spreads apart.

In this position, the pusher 22 is thus held in position by the surgeon while the tube 20 joining the cap 18 is pulled back in the direction of the arrow F1 in order to bring the cap 18 closer to the claws 72 provided at the end of the pusher 22.

Under the action of the pulling of the tube 20, the endpiece 18 approaches the wall 110. The rings 40 of the collar 14 which are formed in the median part of the latter are maintained in the plane of the wall 110 by the pusher 22, and in particular the claws 72 thereof which are engaged in the notches 50 formed at the base of the arms 34. Thus, upon displacement of the endpiece 18, the rings 38 and 40 are moved axially towards each other. As a result of this closing together, the arms 34 of the crown 30 which is engaged inside the first endoprosthesis 108 deform radially away from the axis of the collar 14 in order to reach a final connection position. In particular, each segment 44 of the arms 34 moves away from the connecting rings 38 and 40 in the direction of the arrows F2 and F3 illustrated in FIG. 4. The two segments 44 of each arm are caused to fold in towards one another by plastic deformation of the connection region 46 joining the two successive segments. During deformation of the arms 34, the connecting rings 38, 40 retain a constant diameter.

Thus, as is illustrated in FIG. 5, after displacement of the endpiece 18, each of the arms 34 is folded back on itself, forming a flap, labelled 120, which generally bears against the inner lateral surface of the wall 110.

Upon deformation of the arms 34, under the action of the axial closing-together of the rings 38 and 40, the bridges 36 initially arranged facing one another are superposed along the cylindrical envelope of the collar 14.

After the arms 34 have been shaped to form the flaps 120, the pusher 22 is pulled back by the surgeon so that the claws 72 disengage from the median region of the collar 14. The claws are then displaced to the end of the collar 14 where the tubular skirt 12 is sewn. The pusher 22 is then pushed back again so that the claws 72 engage at the base of the arms 34 of the second crown 32 in the notches 50.

After engagement of the claws 72, and while the tube 20 is being held stationary, thereby guaranteeing immobilization of the endpiece 18, the pusher 22 is again pushed axially towards the endpiece 18 in the direction of the arrow F4 (FIG. 6). This results in the rings 38 and 40 of the crown 32 moving towards each other, leading to plastic deformation of the arms 34 outwards, while the diameter of the rings 38, 40 remains constant.

In a manner analogous to the first crown 30, the second crown 32 deforms plastically so that the segments of each arm 34 fold back against one another to form projecting flaps 122 which can be seen in FIG. 7.

It will be appreciated that after deformation of the arms of the second crown 32, the endoprosthesis is immobilized in relation to the wall 110, the latter being gripped between the flaps 120 and 122.

The pusher 22 is then drawn back by the surgeon exerting traction thereon. The claws 72 disengage from the collar 14 on account of their adapted profile.

After complete withdrawal of the pusher 22, a toroidal balloon 130, illustrated in FIG. 7, is engaged around the radiological guide 24 and the tube 20. The balloon 130 has a length substantially equal to that of the collar 14 after deformation of the arms 34.

The balloon 130 is continued by a conduit 32 for supply of air.

As is illustrated in FIG. 8, the balloon 130 is moved along the tube 20 until it arrives inside the connection collar 14. The endpiece 18 is then disengaged from the collar 14 by pushing on the tube 20. The balloon can already be at a slight overpressure in order to support the flaps 120, 122 during pushing of the tube 20 to disengage the endpiece 18.

While the tube 20 is being pushed, the collar 14 supported by the wall 110 disconnects from the endpiece 18, thereby permitting its release.

As is illustrated in FIG. 9, compressed air is then introduced into the balloon 130 to inflate it. The balloon 130 is designed for radial expansion when inflated.

Figure 10:
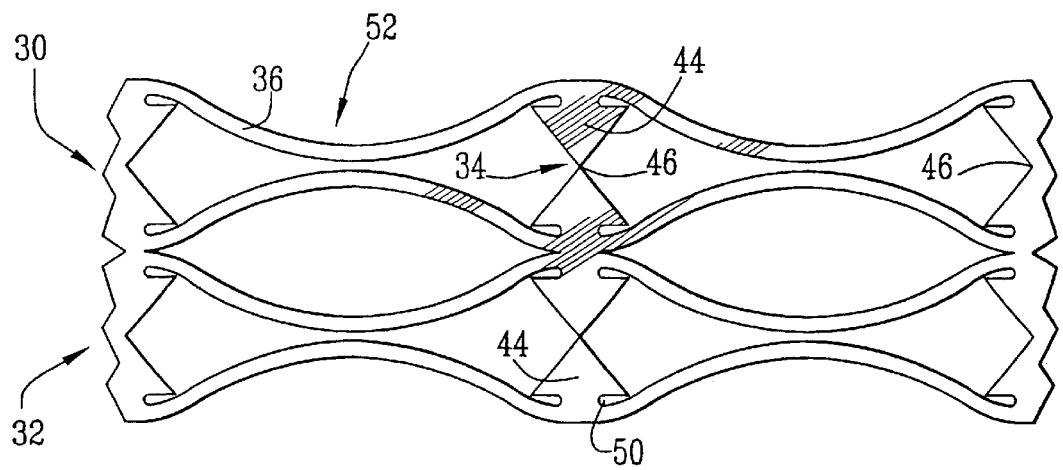
FIG. 10 is a detailed view of a portion of the connection collar after plastic deformation of the securing elements and radial expansion of the collar.

Under the action of this radial expansion, the collar 14 deforms plastically and its diameter increases. In particular, the bridges 36, initially in the form of closed arches, deform and thereby increase the diameter of each of the rings 38 and 40. During this deformation, the bridges 36 open gradually to form arches 52 of very great diameter, as is illustrated in FIG. 10.

The collar 14 is deformed until its internal diameter corresponds substantially to the diameter of the skirt 12, this diameter being substantially equal to that of the first endoprosthesis 108 installed beforehand.

After the collar 14 has been deformed, the balloon 130 is deflated. It is then withdrawn by traction. The diameter of the collar 14 being much greater than its initial diameter, the endpiece 18 can also be withdrawn by traction. The surgical guide 24 is finally withdrawn.

Figure 11:
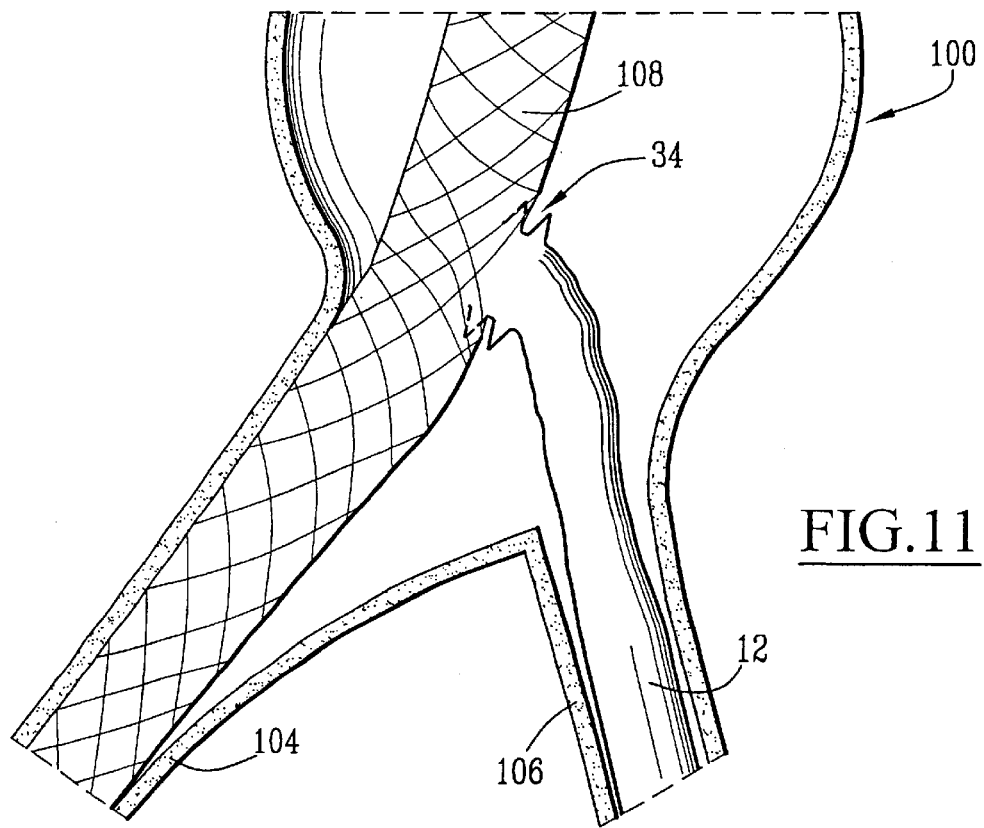
FIG. 11 is a schematic view of the endoprosthesis installed in an aneurysm.

At the end of the intervention, and as is illustrated in FIG. 11, the endoprosthesis 10 is joined to the first endoprosthesis 108 and constitutes a lateral branch of this endoprosthesis.

The presence of the collar 14b which is deformed axially in order to form the flaps 120 and 122 and radially in order to increase its diameter ensures that the skirt 12 is held in place relative to the first endoprosthesis 108.

It will be appreciated that, when the blood flow is re-established, the blood finds itself channelled through the endoprostheses 108 and 10, thereby reducing the pressure applied to the arterial walls in the region of the aneurysm 100.

As the two arms of the final prosthesis consisting of the endoprostheses 10 and 108 are installed in succession, and each through an artery 104 and 106, such a prosthesis is relatively easy for the surgeon to fit.

What is claimed is:

1. An operating kit for celioscopic surgery, said kit comprising:
a tubular endoprosthesis comprising a flexible tubular skirt for channeling a body fluid, and a collar for connecting said flexible tubular skirt through a lateral wall of a tubular conduit,
wherein said connection collar is initially joined to one end of said flexible tubular skirt and has, at its periphery, securing elements for securing it to the wall, and said securing elements are deformable between an initial docking position and a final connection position,
wherein said connection collar has a first crown comprising first and second continuous rings which are centered on the axis of said tubular endoprosthesis and to which securing elements are joined, said second ring comprising bearing contours, and said first and second rings are displaceable axially between a spaced-apart position, in which said securing elements are in the initial docking position, and a closed-together position in which said securing elements are in the final connection position;
a filiform member comprising an end piece for retaining said first ring of said connection collar; and
a filiform pusher comprising claws for engaging in the bearing contours of said second ring of said connection collar,
wherein said filiform pusher and said filiform member are axially slidable to displace said first and second rings from their spaced-apart position to their closed-together position.

2. The kit as claimed in claim 1, wherein said connection collar comprises a second crown axially spaced apart from said first crown, said second crown comprising said second ring and a third continuous ring centered on the axis of said tubular endoprosthesis, said second crown comprising securing elements connected to said second and third rings, said third ring comprising bearing contours for engaging the claws of said filiform pusher, wherein said second and third rings are displaceable axially between a spaced-apart position, in which said securing elements are in their initial docking position, and a closed-together position in which said securing elements are in their final connection position and the claws are adapted to disengage from the bearing contours of said second ring to be engaged in the bearing contours of said third ring.

3. The kit as claimed in claim 2, wherein said securing elements are adapted to bear against a face of the lateral wall of the tubular conduit in their final connection position.

4. The kit as claimed in claim 3, wherein said securing elements are elements which are plastically deformable from their initial docking position to their final connection position.

5. The kit as claimed in claim 3, wherein said securing elements are elements that are capable of centrifugal radial expansion from their initial docking position to their final connection position.

6. The kit as claimed in 3, wherein said connection collar includes plastically deformable bridges capable of permitting radial expansion of said connection collar from a first configuration, in which said connection collar has an initial diameter, to a second configuration in which said connection collar has a diameter that is greater than the initial diameter of said connection collar.

7. The kit as claimed in claim 3, further comprising a toroidal inflatable balloon capable of radial expansion.

8. The kit as claimed in claim 3, further comprising another endoprosthesis intended to form the tubular conduit to which the tubular endoprosthesis is to be secured.

9. The kit as claimed in claim 2, wherein said securing elements are elements which are plastically deformable from their initial docking position to their final connection position.

10. The kit as claimed in claim 2, wherein said securing elements are elements that are capable of centrifugal radial expansion from their initial docking position to their final connection position.

11. The kit as claimed in claim 2, further comprising a toroidal inflatable balloon capable of radial expansion.

12. The kit as claimed in claim 2, further comprising another endoprosthesis intended to form the tubular conduit to which the tubular endoprosthesis is to be secured.

13. The kit as claimed in claim 1, wherein said securing elements are adapted to bear against a face of the lateral wall of the tubular conduit in their final connection position.

14. The kit as claimed in claim 1, wherein said securing elements are elements which are plastically deformable from their initial docking position to their final connection position.

15. The kit as claimed in claim 14, wherein said securing elements are elements that are capable of centrifugal radial expansion from their initial docking position to their final connection position.

16. The kit as claimed in claim 14, wherein said connection collar includes plastically deformable bridges capable of permitting radial expansion of said connection collar from a first configuration, in which said connection collar has an initial diameter, to a second configuration in which said connection collar has a diameter that is greater than the initial diameter of said connection collar.

17. The kit as claimed in claim 14, further comprising a toroidal inflatable balloon capable of radial expansion.

18. The kit as claimed in claim 14, further comprising another endoprosthesis intended to form the tubular conduit to which the tubular endoprosthesis is to be secured.

19. The kit as claimed in claim 1, wherein said securing elements are elements that are capable of centrifugal radial expansion from their initial docking position to their final connection position.

20. The kit as claimed in claim 19, wherein each securing element comprises an arm having two consecutive segments joined to one another via a region of articulation, and wherein each arm is deformable from an initial docking position, in which the two segments are spaced apart and extend substantially along a generatrix of said tubular endoprosthesis, to a final connection position in which the two segments are folded in towards one another.

21. The kit as claimed in claim 20, wherein said connection collar includes plastically deformable bridges capable of permitting radial expansion of said connection collar from a first configuration, in which said connection collar has an initial diameter, to a second configuration in which said connection collar has a diameter that is greater than the initial diameter of said connection collar.

22. The kit as claimed in claim 20, further comprising another endoprosthesis intended to form the tubular conduit to which the tubular endoprosthesis is to be secured.

23. The kit as claimed in 19, wherein said connection collar includes plastically deformable bridges capable of permitting radial expansion of said connection collar from a first configuration, in which said connection collar has an initial diameter, to a second configuration in which said connection collar has a diameter that is greater than the initial diameter of said connection collar.

24. The kit as claimed in claim 19, further comprising a toroidal inflatable balloon capable of radial expansion.

25. The kit as claimed in claim 19, further comprising another endoprosthesis intended to form the tubular conduit to which the tubular endoprosthesis is to be secured.

26. The kit as claimed in 1, wherein said connection collar includes plastically deformable bridges capable of permitting radial expansion of said connection collar from a first configuration, in which said connection collar has an initial diameter, to a second configuration in which said connection collar has a diameter that is greater than the initial diameter of said connection collar.

27. The kit as claimed in claim 26, wherein said plastically deformable bridges each have a general arch shape and extend along the periphery of said connection collar, wherein said bridges are deformable from an initial position, in which each arch is closed and said connection collar is in the first configuration, and a final position in which each arch is opened and said connection collar is in the second configuration.

28. The kit as claimed in claim 26, further comprising another endoprosthesis intended to form the tubular conduit to which the tubular endoprosthesis is to be secured.

29. The kit as claimed in 2, wherein said connection collar includes plastically deformable bridges capable of permitting radial expansion of said connection collar from a first configuration, in which said connection collar has a initial diameter, to a second configuration in which said connection collar has a diameter that is greater than the initial diameter of said connection collar.

30. The kit as claimed in claim 1, further comprising a toroidal inflatable balloon capable of radial expansion.

31. The kit as claimed in claim 1, further comprising another endoprosthesis intended to form the tubular conduit to which the tubular endoprosthesis is to be secured.

* * * * *

UNITED STATES PATENT AND TRADEMARK OFFICE
CERTIFICATE OF CORRECTION

PATENT NO. : 6,827,736 B2
DATED : December 7, 2004
INVENTOR(S) : Eric Perouse

It is certified that error appears in the above-identified patent and that said Letters Patent is hereby corrected as shown below:

<u>Title page,</u>
Item [73], Assignee, change "Laboratories Perouse" to -- Laboratoires Perouse --.

Signed and Sealed this

Fifteenth Day of March, 2005

JON W. DUDAS
*Director of the United States Patent and Trademark Office*